US009581582B2

(12) United States Patent
Walloch et al.

(10) Patent No.: US 9,581,582 B2
(45) Date of Patent: Feb. 28, 2017

(54) TRACERS FOR DETECTING THE PRESENCE OF SOLID ADMIXTURES

(71) Applicant: ACM Chemistries, Inc., Norcross, GA (US)

(72) Inventors: Craig T. Walloch, Norcross, GA (US); Theodore G. Light, Suwanee, GA (US); Marshall L. Brown, Berkeley Lake, GA (US); Matthew J. Oesterle, Flowery Branch, GA (US)

(73) Assignee: ACM Chemistries, Inc., Norcross, GA (US)

( * ) Notice: Subject to any disclaimer, the term of this patent is extended or adjusted under 35 U.S.C. 154(b) by 432 days.

(21) Appl. No.: 13/687,328

(22) Filed: Nov. 28, 2012

(65) Prior Publication Data
US 2013/0145827 A1  Jun. 13, 2013

Related U.S. Application Data

(60) Provisional application No. 61/565,341, filed on Nov. 30, 2011.

(51) Int. Cl.
*G01N 33/38* (2006.01)
*G01N 23/223* (2006.01)

(52) U.S. Cl.
CPC ......... *G01N 33/383* (2013.01); *G01N 23/223* (2013.01)

(58) Field of Classification Search
CPC ....... G01N 33/38; G01N 23/223; G01N 33/28
USPC .............................................. 73/53.01–64.56
See application file for complete search history.

(56) References Cited

U.S. PATENT DOCUMENTS

| | | | | |
|---|---|---|---|---|
| 3,557,015 A * | 1/1971 | Alburger | .................. | 252/301.19 |
| 3,565,533 A * | 2/1971 | Garcia | ................ | C04B 40/0042 106/712 |
| 3,615,223 A * | 10/1971 | Burrqughs et al. | ........... | 356/409 |
| 4,003,431 A * | 1/1977 | Novotny et al. | ............... | 166/293 |
| 4,196,614 A * | 4/1980 | McLaughlin | ................ | 73/61.41 |
| 4,686,852 A * | 8/1987 | Ito et al. | ....................... | 73/61.72 |
| 4,843,868 A * | 7/1989 | Propst | ......................... | 73/61.72 |
| 5,237,858 A * | 8/1993 | Ohsaki et al. | ................ | 73/61.72 |
| 5,324,356 A * | 6/1994 | Goodwin | ............ | C04B 40/0096 106/638 |
| 5,410,152 A * | 4/1995 | Gadeken | ................. | E21B 43/04 250/259 |

(Continued)

*Primary Examiner* — Daniel S Larkin
*Assistant Examiner* — Nathaniel Kolb
(74) *Attorney, Agent, or Firm* — Altera Law Group, LLC

(57) ABSTRACT

In some variations, this disclosure provides a method of verifying the presence of an admixture in association with a solid base material, by combining the admixture with a stable inorganic tracer. A sample of the solid base material may be analyzed, using suitable analytical techniques, to detect the presence of the inorganic tracer in excess of any native inorganic tracer. When the inorganic tracer is positively detected, it is confirmed that the traceable admixture has been properly dosed within the base material. The inorganic tracer may comprise a rare earth metal, such as selenium, molybdenum, bismuth, and combinations, alloys, or oxides thereof, for example. The solid base material may be a cementitious material, in some embodiments. The traceable admixture may be a water-repellent admixture, in some embodiments. The principles of the invention, however, are widely applicable.

20 Claims, 3 Drawing Sheets

| Amount of $Bi_2O_3$ added to Dry-Mortar | Amount of Bi added to Dry-Mortar | Amount of Bi in cured hardened mortar (96% of total w/o hydration) | Analytical ICP/MS Results | Actual - Predicted | |
|---|---|---|---|---|---|
| 0 | 0 | 0 | 0.5 | 0.5 | |
| 18.7 | 18.7 | 16.1 | 17 | 0.9 | |
| 37.3 | 33.5 | 32.1 | 28 | -4.1 | Chicago Portland |
| 56.0 | 50.2 | 48.2 | 50 | 1.8 | Cement/Lime |
| 74.7 | 67.0 | 64.3 | 66 | 1.7 | Mortar |
| 93.3 | 83.7 | 80.4 | 78 | -2.4 | |
| 0.0 | 0.0 | 0.0 | 0 | 0.0 | |
| 18.7 | 16.7 | 16.1 | 17 | 0.9 | |
| 37.3 | 33.5 | 32.1 | 32 | -0.1 | |
| 37.3 | 33.5 | 32.1 | 34 | 1.9 | TN Masonry |
| 37.3 | 33.5 | 32.1 | 36 | 3.9 | Cement Mortar |
| 56.0 | 50.2 | 48.2 | 53 | 4.8 | |
| 74.7 | 67.0 | 64.3 | 62 | -2.3 | |
| 93.3 | 83.7 | 80.4 | 85 | 4.6 | |

| | |
|---|---|
| Average | 0.9 |
| Average Deviation | 1.9 |
| Maximum | 4.8 |
| Minimum | -4.1 |

(56) References Cited

U.S. PATENT DOCUMENTS

| | | | |
|---|---|---|---|
| 5,460,648 A | 10/1995 | Walloch | |
| 6,165,248 A * | 12/2000 | Leiner | C22B 1/005 |
| | | | 436/80 |
| 7,765,883 B1 * | 8/2010 | Spangle | 73/866 |
| 7,804,406 B2 * | 9/2010 | Kaga et al. | 340/572.1 |
| 8,032,244 B2 * | 10/2011 | Trost et al. | 700/109 |
| 8,764,272 B2 * | 7/2014 | Hazrati et al. | 366/2 |
| 2002/0005149 A1 * | 1/2002 | Karkare | C04B 24/08 |
| | | | 106/808 |
| 2003/0196799 A1 * | 10/2003 | Nguyen | C09K 8/805 |
| | | | 166/250.12 |
| 2004/0064265 A1 * | 4/2004 | Myers et al. | 702/32 |
| 2011/0011161 A1 * | 1/2011 | Turpin, Jr. | 73/29.02 |
| 2012/0004776 A1 * | 1/2012 | Abad | 700/265 |

\* cited by examiner

FIG. 1

| Amount of Bi$_2$O$_3$ added to Dry-Mortar | Amount of Bi added to Dry-Mortar | Amount of Bi in cured hardened mortar (96% of total w/o hydration) | Analytical ICP/MS Results | Actual - Predicted | |
|---|---|---|---|---|---|
| 0 | 0 | 0 | 0.5 | 0.5 | |
| 18.7 | 16.7 | 16.1 | 17 | 0.9 | |
| 37.3 | 33.5 | 32.1 | 28 | -4.1 | Chicago Portland Cement/Lime Mortar |
| 56.0 | 50.2 | 48.2 | 50 | 1.8 | |
| 74.7 | 67.0 | 64.3 | 66 | 1.7 | |
| 93.3 | 83.7 | 80.4 | 78 | -2.4 | |
| 0.0 | 0.0 | 0.0 | 0 | 0.0 | |
| 18.7 | 16.7 | 16.1 | 17 | 0.9 | |
| 37.3 | 33.5 | 32.1 | 32 | -0.1 | |
| 37.3 | 33.5 | 32.1 | 34 | 1.9 | TN Masonry Cement Mortar |
| 37.3 | 33.5 | 32.1 | 36 | 3.9 | |
| 56.0 | 50.2 | 48.2 | 53 | 4.8 | |
| 74.7 | 67.0 | 64.3 | 62 | -2.3 | |
| 93.3 | 83.7 | 80.4 | 85 | 4.6 | |

|  |  |
|---|---|
| Average | 0.9 |
| Average Deviation | 1.9 |
| Maximum | 4.8 |
| Minimum | -4.1 |

FIG. 2

| Amount of Bi in cured hardened mortar (96% of total w/o hydration) | Linear Regression Amount of Bi in cured hardened mortar (96% of total w/o hydration) |
|---|---|
| 0 | 0.6 |
| 16.1 | 16.8 |
| 32.1 | 33.0 |
| 48.2 | 49.1 |
| 64.3 | 65.3 |
| 80.4 | 81.5 |
| 0.0 | 0.6 |
| 16.1 | 16.8 |
| 32.1 | 33.0 |
| 32.1 | 33.0 |
| 32.1 | 33.0 |
| 48.2 | 49.1 |
| 64.3 | 65.3 |
| 80.4 | 81.5 |
| Slope | 1.0072 |
| Intercept | 0.5753 |
| $R^2$ | 0.9906 |

TRACERS FOR DETECTING THE PRESENCE OF SOLID ADMIXTURES

PRIORITY DATA

This patent application claims priority to U.S. Patent App. No. 61/565,341, filed Nov. 30, 2011, which is hereby incorporated by reference herein in its entirety.

FIELD

This disclosure relates to methods for detecting and quantifying solid admixtures in base materials, such as cementitious materials.

BACKGROUND

Water-repellent additives have been incorporated into hydraulic cement-based products for decades, serving to resist moisture, such as rain water, from penetrating excessively into materials, such as masonry mortars. Reducing moisture penetration can help to resist mold and mildew, to protect against cracks, and to resist efflorescence stains. Reducing water absorption also prevents or minimizes the damaging effects of freeze-thaw cycles.

Although these water-repellent additives to cementitious materials have been relatively effective, their chemical composition is very similar to the chemical composition of the hydraulic cement materials to which they are added. There are occasions when the water-repellent additives are not added or in improper amounts, either in error or deliberately. Therefore, it would be important to be able to detect the presence of a properly formulated mixture during construction, and certainly before it is too late take corrective action. Furthermore, the ability to test for compliance may be a strong incentive to comply with the specified formulations.

Heretofore, water-repellent additives were not intended to be detected or quantified once the cementitious material has hardened. The evaluator is often relegated to attempt some kind of physical property measurement, such as a water uptake test or complicated and expensive analytical test. Such tests often are not very reliable for determining whether the water-repellent additive is present or for estimating whether the water-repellent additive has been added at a sufficient dosage and distribution (i.e., well-dispersed throughout the cement-based material) especially when conducted on hardened masonry mortar samples removed from a wall because of the small dimensions of the samples which are typically only ⅜ inch (10 mm) in width by 1 to 1.5 inch (25 to 40 mm) in depth.

Due to the difficulty with the prior formulations of water-repellent admixtures, organizations such as the National Concrete Masonry Association and ASTM have not recognized an analytical technique for identifying or measuring the presence of a water-repellent additive in cementitious materials, such as masonry mortar. The typical technique is to directly evaluate the level of water repellency exhibited by the cement-based material, but that is difficult due to small sample sizes that are necessary in most situations. What is desired is a method to indirectly detect and quantify the presence of the water-repellent admixture without needing to test the water repellency.

It would be beneficial to employ a tracer that can indirectly verify the presence, quantity, and/or distribution of water-repellent admixture within a cement-based material. What is needed is a tracer additive that is reliably identifiable, qualitatively and/or quantitatively, after the hydraulic cement-based material has aged and weathered over time. Desirable tracers would not oxidize and degrade over time.

SUMMARY OF THE DISCLOSURE

This summary is provided to assist the reader in understanding the full disclosure but is not a limitation of that disclosure. The claims define the scope of the invention.

In some variations, this disclosure provides a method of verifying the presence of an admixture in association with a solid base material, the method comprising:

(a) providing an admixture suitable for combining with a solid base material;

(b) providing an inorganic tracer that is substantially water-insoluble and stable in the presence of the admixture and the solid base material;

(c) combining the admixture and the inorganic tracer to form a traceable admixture;

(d) obtaining a sample comprising the solid base material; and (e) analyzing the sample for the presence of the traceable admixture, by detecting the inorganic tracer, if present in the sample in excess of any native inorganic tracer associated with the solid base material.

When the inorganic tracer is positively detected within the sample, confirmation is obtained that a step of combining the traceable admixture with the solid base material has been performed. When the inorganic tracer is quantified within the sample, it may be indicated that a proper amount of the traceable admixture has been combined with the solid base material. When the inorganic tracer is detected or quantified within the sample and within at least one additional sample, it may be indicated that a proper distribution of the traceable admixture has been introduced within the solid base material.

In some embodiments, the inorganic tracer is detectable by inductively coupled plasma, which may be configured with an atomic-emissions spectroscopy detector or a mass-spectroscopy detector, for example. In these or other embodiments, the inorganic tracer is detectable by flame atomic absorption, energy-dispersive X-ray spectroscopy, by X-ray fluorescence spectrometry, or an electron-probe microanalyzer.

In some embodiments, the inorganic tracer comprises one or more rare earth metals or precious metals. In certain embodiments, the inorganic tracer is selected from the group consisting of selenium, molybdenum, bismuth, and combinations and alloys thereof. The inorganic tracer may consist essentially of selenium, molybdenum, or bismuth.

In some embodiments, the inorganic tracer is selected from an oxide, hydride, sulfide, or carbide of an element selected from the group consisting of selenium, molybdenum, bismuth, and combinations thereof. For example, the inorganic tracer may consist essentially of bismuth trioxide. In alternative embodiments, wherein the inorganic tracer comprises titanium and/or titanium dioxide.

The inorganic tracer may be present in the traceable admixture is a concentration of about 50 wt % or less. In some embodiments, the inorganic tracer is present in the traceable admixture is a concentration of about 20 wt % or less, such as about 10 wt % or less or about 5 wt % or less.

Preferably, the inorganic tracer is present in the traceable admixture in a concentration that is at least two, five, or ten times the native concentration of the inorganic tracer, if any, in the solid base material.

In some embodiments, the inorganic tracer comprises molybdenum in an amount from about 0.1 wt % to about 20 wt % of the traceable admixture, such as from about 1 wt % to about 10 wt % of the traceable admixture.

In some embodiments, the inorganic tracer comprises bismuth trioxide present in an amount from about 0.1 wt % to about 20 wt % of the traceable admixture, such as from about 1 wt % to about 10 wt % of the traceable admixture.

The presence of the inorganic tracer preferably does not substantially alter the mechanical properties of the solid base material. In some embodiments, the solid base material comprises a cementitious material, optionally further comprising an aggregate. The presence of the inorganic tracer should not substantially alter the mechanical properties of the cementitious material or the mortar.

The traceable admixture may be a solid water-repellent admixture or a liquid water-repellent admixture. When the base material is a cementitious material, the inorganic tracer is preferably stable in alkaline conditions that are typically present.

While the discussion which follows relates to inorganic tracers, they may also be organic or unstable provided that the tracer is detectable at the time of installation, whereafter the presence of the tracer can be certified and thereafter it may disintegrate or otherwise disappear. Therefore, all references to inorganic tracers are deemed to also include organic tracers or materials which may ultimately disintegrate or disappear over time.

Some variations provide a method of verifying the presence of a water-repellent admixture in association with a cementitious material, the method comprising:

(a) providing a water-repellent admixture suitable for combining with a cementitious material;

(b) providing an inorganic tracer that is substantially water-insoluble and stable in the presence of the water-repellent admixture and the cementitious material;

(c) combining the water-repellent admixture and the inorganic tracer to form a traceable water-repellent admixture;

(d) obtaining a sample comprising the cementitious material, in uncured or cured form; and (e) analyzing the sample for the presence of the traceable admixture, by detecting the inorganic tracer, if present in the sample in excess of any native inorganic tracer associated with the cementitious material;

wherein positive detection of the inorganic tracer within the sample indicates that a step of combining the traceable admixture with the cementitious material has been performed.

Some variations provide a method of verifying the presence of an admixture, the method comprising:

(a) providing a water-repellent admixture suitable for combining with a base material;

(b) providing an inorganic tracer that is substantially water-insoluble and stable in the presence of the admixture and the base material;

(c) combining the admixture and the inorganic tracer to form a traceable admixture;

(d) obtaining a sample that may contain the traceable admixture; and (e) analyzing the sample for the presence of the traceable admixture, by detecting the inorganic tracer, if present in the sample in excess of any native inorganic tracer associated with the admixture.

Some variations provide a method of verifying the presence of a water-repellent admixture in association with a mortar or mortar mix, the method comprising:

(a) providing or generating a traceable water-repellent admixture comprising a water-repellent admixture and an inorganic tracer, wherein the inorganic tracer is substantially water-insoluble and stable in the presence of the water-repellent admixture and the mortar or mortar mix;

(b) obtaining a sample comprising the mortar or mortar mix, in uncured or cured form; and (c) analyzing the sample for the presence of the traceable water-repellent admixture, by detecting the inorganic tracer, if present in the sample in excess of any native inorganic tracer associated with the mortar or mortar mix, wherein positive detection of the inorganic tracer in excess of native inorganic tracer within the sample indicates that the water-repellent admixture is included in the mortar or mortar mix.

Some variations provide a method of verifying the presence of a water-repellent admixture in association with a pre-blended dry mortar mix, the method comprising:

(a) providing a water-repellent admixture suitable for combining with a dry mortar;

(b) providing an inorganic tracer that is substantially water-insoluble and stable in the presence of the water-repellent admixture and the dry mortar;

(c) combining the water-repellent admixture and the inorganic tracer to form a traceable water-repellent admixture;

(d) obtaining a sample comprising the dry mortar; and (e) analyzing the sample for the presence of the traceable admixture, by detecting the inorganic tracer, if present in the sample in excess of any native inorganic tracer associated with the dry mortar.

Some variations provide a method of verifying the presence of a water-repellent admixture in association with a masonry mortar, the method comprising:

(a) providing a water-repellent admixture suitable for a masonry mortar;

(b) providing an inorganic tracer that is substantially water-insoluble and stable in the presence of the water-repellent admixture and the masonry mortar;

(c) combining the water-repellent admixture and the inorganic tracer to form a traceable water-repellent admixture;

(d) obtaining a sample comprising the masonry mortar; and (e) analyzing the sample for the presence of the traceable admixture, by detecting the inorganic tracer, if present in the sample in excess of any native inorganic tracer associated with the masonry mortar.

Some variations provide a method of verifying the presence of a water-repellent admixture in association with a cured hardened mortar, the method comprising:

(a) providing a water-repellent admixture suitable for a hardened mortar;

(b) providing an inorganic tracer that is substantially water-insoluble and stable in the presence of the water-repellent admixture and the hardened mortar;

(c) combining the water-repellent admixture and the inorganic tracer to form a traceable water-repellent admixture;

(d) obtaining a sample comprising the hardened mortar; and (e) analyzing the sample for the presence of the traceable admixture, by detecting the inorganic tracer, if present in the sample in excess of any native inorganic tracer associated with the hardened mortar.

Some variations provide a traceable admixture (composition) comprising an inorganic tracer and a solid admixture for a cementitious material, wherein the inorganic tracer is substantially water-insoluble and stable in alkaline conditions. The traceable admixture may be a solid or liquid water-repellent admixture.

In some embodiments, the inorganic tracer is detectable by a technique selected from the group consisting of inductively coupled plasma, inductively coupled plasma configured with an atomic-emission spectroscopy detector or a mass-spectroscopy detector, flame atomic absorption, energy-dispersive X-ray spectroscopy, X-ray fluorescence spectrometry, and electron-probe microanalysis.

In some embodiments, the inorganic tracer comprises one or more rare earth metals, such as (but not limited to) selenium, molybdenum, bismuth, or combinations and alloys thereof. In some embodiments, the inorganic tracer consists essentially of selenium, molybdenum, or bismuth. In certain embodiments, the inorganic tracer is selected from an oxide, hydride, sulfide, or carbide of an element selected from the group consisting of selenium, molybdenum, bismuth, and combinations thereof, such as bismuth trioxide.

The inorganic tracer may be present in the admixture in a concentration of about 20 wt % or less, such as about 10 wt %, about 5 wt %, or less. In some embodiments, the inorganic tracer comprises molybdenum in an amount from about 0.1 wt % to about 20 wt % of the admixture, such as from about 1 wt % to about 10 wt % of the admixture. In some embodiments, the inorganic tracer comprises bismuth trioxide present in an amount from about 0.1 wt % to about 20 wt % of the admixture, such as from about 1 wt % to about 10 wt % of the admixture.

In some embodiments, the inorganic tracer is present in the admixture in a concentration that is at least 2, 3, 4, 5, or 10 times the native concentration of the inorganic tracer, if any, in the cementitious material.

Some embodiments provide a traceable water-repellent admixture containing an inorganic tracer and one or more materials selected from the group consisting of silanes, siloxanes, free fatty acids, fatty acid derivatives, and particulated polymers or copolymers.

The traceable water-repellent admixture may be used in various ways. Some embodiments provide a cementitious material comprising, or in association with, a traceable admixture. Some embodiments provide a pre-blended dry mortar mix comprising a traceable admixture as disclosed herein. Some embodiments provide a masonry mortar comprising a traceable admixture. Some embodiments provide a cured hardened mortar comprising a traceable admixture as disclosed.

BRIEF DESCRIPTION OF THE FIGURES

FIG. 1 shows experimental data of bismuth amount in mortar samples, according to Example 1.

FIG. 2 shows statistical data relating to the experimental data of bismuth amount in mortar samples, according to Example 1.

DETAILED DESCRIPTION OF SOME EMBODIMENTS

Figure 3:
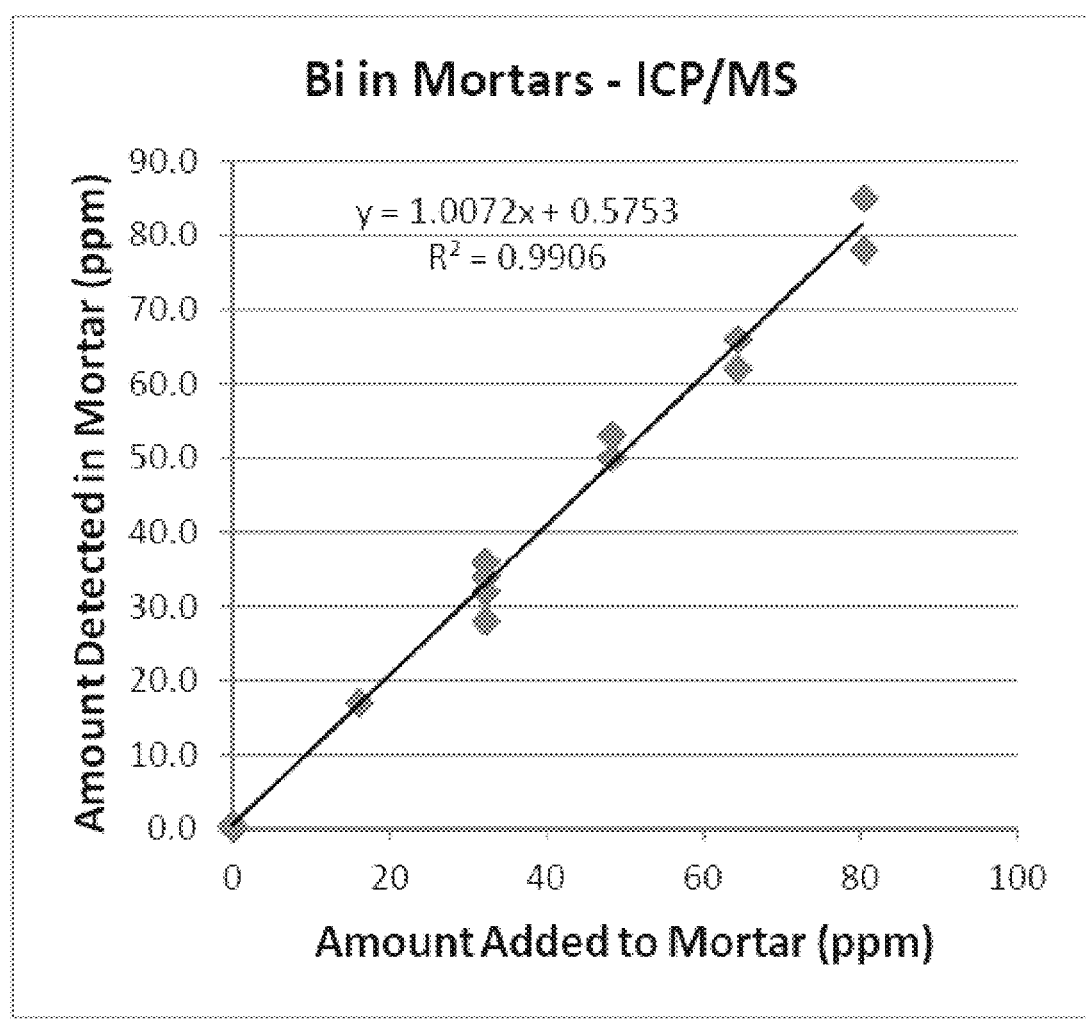
FIG. 3 plots actual versus predicted amounts of bismuth tracer, according to Example 1.

This description will enable one skilled in the art to make and use the principles of the disclosure, and it describes several embodiments, adaptations, variations, alternatives, and uses of the disclosure.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. As used herein, a "composition," "blend," "admixture," "admix," or "mixture" are all intended to be used interchangeably.

Unless otherwise indicated, all numbers expressing parameters, conditions, concentrations, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

Some variations are directed to admixtures intended for cementitious materials. As intended herein, an "admixture" means any composition that, when combined with a base material, enhances a selected property of the base material under conditions of use. An example is a water-repellent admixture for a cementitious material to improve the water repellency.

Cementitious materials are typically building materials which may be mixed with a liquid, such as water, to form a plastic paste, and to which an aggregate may be added in any amount. As intended herein, a "cementitious material" is broadly construed as any cement-based mixture, mortar, or the like; with or without water; and before, during, or after curing or setting into a hardened, structural material. Cementitious materials include Portland cement, limes, masonry cement, mortar cement, blended cement, slag cement, fly ash and other pozzolanic materials, and masonry mortar, for example.

Some variations provide methods of incorporating a traceable, inorganic ingredient into an admixture, where the traceable ingredient (or "tracer") provides easy verification of whether the traceable admixture has been properly added to a base material, such as a hydraulic cement-based product. The invention is by no means limited to cement-based products or to water-repellent admixtures. The principles disclosed herein have general applicability.

While the discussion which follows relates to inorganic tracers, they may also be organic or unstable provided that the tracer is detectable at the time of installation, whereafter the presence of the tracer can be certified and thereafter it may disintegrate or otherwise disappear. Therefore, all references to inorganic tracers are deemed to also include organic tracers or materials which may ultimately disintegrate or disappear over time.

In some variations, a method of verifying the presence of an admixture in association with a solid base material, comprises:

(a) providing an admixture suitable for combining with a solid base material;

(b) providing an inorganic tracer that is substantially water-insoluble and stable in the presence of the admixture and the solid base material;

(c) combining the admixture and inorganic tracer to form a traceable admixture;

(d) obtaining a sample comprising the solid base material; and (e) analyzing the sample for the presence of the traceable admixture, by detecting the inorganic tracer, if present in the sample in excess of any native inorganic tracer associated with the solid base material.

Some embodiments provide a water-repellent admixture for hydraulic cement-based materials in which it can be verified that the admixture was added properly. By incorporating an inorganic tracer within cement-based materials, wherein the tracer has the ability to remain sufficiently bound indefinitely within the cementitious material matrix, a laboratory technician or researcher may reliably identify the ingredient and quantify its presence. By quantifying the tracer concentration within the cementitious material and correlating it to the amount of the admixture formulation, one can determine if the cement-based material was properly dosed with an admixture (e.g., a water-repellent admixture) as specified for a project. Proper dosage includes both the quantity (concentration) of the admixture, as well as the distribution throughout the cement-based material.

Water-repellent additives that are typically used to impart hydrophobic properties to cement-based materials are not easily detected using petrographic or chemical-analysis techniques. Inorganic tracers provide for a method to quantifiably detect the presence of a water-repellent or other type of additive.

This disclosure contemplates any suitable inorganic material as a tracer that is not water-soluble and is stable in the alkaline conditions of a cement-based material. While the tracer may be added at any dosage rate that preferably does not adversely affect the properties of the plastic or hardened mortar, preferably the tracer is added at a level that is less than about 20% of the water-repellent admixture weight, for economic reasons. Low levels of tracers are generally desired, as long as they are detectable by suitable analytical techniques.

Analytical techniques for detecting inorganic tracers include, but are not limited to, inductively coupled plasma (ICP) optionally with an atomic emission spectroscopy detector (ICP-AES) or a mass spectroscopy detector (ICP-MS), flame atomic absorption (AA), energy-dispersive X-ray spectroscopy (EDX), X-ray fluorescence spectrometry (XFS), and electron-probe microanalysis.

Suitable techniques can typically detect inorganic tracers down to 1 ppm or less. Preferably, the inorganic tracer is present in a sample (e.g., a hardened mortar) at a level of about 5 ppm, 10 ppm, 20 ppm, 30 ppm, 40 ppm, 50 ppm, 100 ppm, 150 ppm, 200 ppm, 300 ppm, 500 ppm, 750 ppm, 900 ppm, or higher, of the sample.

For traceable admixtures intended for cement-based materials, it is important to select a tracer that has a low natural abundance in the earth's crust, in general, and in mortar materials (cementitious materials and aggregates) in particular. Preferably, the inorganic tracer is present in the traceable admixture in a concentration that is at least 2, 5, or 10 times the native concentration of the inorganic tracer, if any, in the solid base material.

The rare-earth metals are particularly suitable because of their low natural abundance. Suitable rare-earth metals include bismuth, molybdenum, selenium, and alloys thereof. The inorganic tracer may be selected from an oxide, hydride, sulfide, or carbide of an element selected from the group consisting of selenium, molybdenum, bismuth, and combinations thereof. For example, the inorganic tracer may consist essentially of bismuth trioxide.

In some embodiments, the inorganic tracer comprises one or more precious metals. In some embodiments, the inorganic tracer comprises titanium and/or titanium dioxide.

The inorganic tracer may be present in the traceable admixture is a concentration of about 50 wt % or less, such as about 20% wt %, 10 wt %, 5 wt %, or less. The concentration of tracer within the final material will depend on how much admixture is added to the base material. In certain embodiments, between about 1 wt % and 10 wt % inorganic tracer is used in the admixture.

Some variations provide a formulation of a solid, traceable water-repellent admixture comprising one or more hydrophobic components that, when added to a cement-based masonry mortar, imparts a degree of water repellency. The traceable water-repellent admixture may be in a powdered form of various particle sizes and shapes. In some embodiments, the traceable water-repellent admixture is a dry, fine powder. In certain embodiments, the traceable water-repellent admixture is a dry mixture of fine powder and coarse particles, which may be pellets, spheres, or random shapes. In some embodiments, the traceable water-repellent admixture is in a solid-liquid slurry, gel, emulsion, or other form in which the solid does not completely dissolve.

Preferably, the degree of water repellency that is attained when the traceable water-repellent admixture is added to a cement-based masonry mortar, complies with the performance set forth in ASTM C1384, Standard Specification for Admixtures for Masonry Mortars, which is incorporated by reference herein.

Preferably, water repellency is achieved by the traceable water-repellent admixture while avoiding a significant change in the air content of the cement-based material. By not significantly changing the air content, the workability of the plastic mortar as well as the properties of the hardened mortar including the compressive strength of the mortar and the bond strength of the mortar to other substrates, such as clay or concrete masonry units, are not adversely affected.

In some embodiments, the traceable water-repellent admixture contains one or more materials selected from silanes, siloxanes, fatty acids, fatty acid derivatives (such as fatty acid salts), or particulated polymers.

Silanes as intended herein are alkyloxysilane chemical compounds of silicon, carbon, oxygen, and hydrogen. The general formula of an alkyloxysilane is $(R_1O)_nSi(R_2)_{4-n}$, where $R_1$ is a linear or branched $C_1$-$C_3$ alkyl, n equals 1 to 3, and $R_2$ is a linear or branched $C_1$-$C_{20}$ alkyl, or phenyl. Exemplary silanes include, but are not limited to, trimethoxy (octyl)silane, triethoxy(octyl)silane, triethoxy(capryl)silane, and triethoxy(vinyl)silane.

Siloxanes are chemical compounds composed of units of the form $R_2SiO$, consisting of alternating silicon and oxygen atoms, with side chains R attached to the silicon atoms. Each R group is independently a hydrogen atom, a hydrocarbon group, or a halogen atom (such as chlorine). When at least one of the R groups is organic, the organic side chain confers hydrophobic properties while the —Si—O—Si—O— backbone is purely inorganic. Exemplary siloxanes include, but are not limited to, hexamethyldisiloxane, hexamethylcyclotrisiloxane, octamethyltrisiloxane, decamethyltetrasiloxane, and polydimethylsiloxane.

A fatty acid is a carboxylic acid with a long unbranched aliphatic tail (chain), which is either saturated or unsaturated. Most naturally occurring fatty acids have a chain of an even number of carbon atoms, from $C_4$ to $C_{28}$. Fatty acids may be derived from triglycerides or phospholipids. When they are not attached to other molecules, fatty acids are known as free fatty acids. Fatty acids may also form fatty acid derivatives of the following formula:

$$R_{FA}COO—A$$

wherein $R_{FA}$ is a $C_7$-$C_{29}$ alkyl(ene) group; and wherein A is H, a $C_1$-$C_{12}$ linear or branched alkyl group, an alkali or alkaline earth metal cation, a polyvalent cation, or a $C_1$-$C_{12}$ linear or branched alkyl or alkanol amine. In certain embodiments, the fatty acids, or derivatives thereof, may include saturated or unsaturated $C_{12}$-$C_{24}$ fatty acids, such as $C_{16}$-$C_{18}$ fatty acids.

Fatty acid derivatives for use in compositions include those described in the published US patent application of Karkare, Patent App. Pun. No. 2002/0005149 A1 and in U.S. Pat. No. 5,460,648 to Walloch.

In some embodiments, the traceable water-repellent admixture contains one or more materials selected from particulated polymers. Examples of particulated polymers include, but are not limited to, polyepoxide, polystyrene-butadiene, polyvinyl acetate, polyacrylonitile-butadiene, polyacrylic ester, polyvinylidene chloride-vinyl chloride, polyethylene-vinylacetate, polyurethane, acrylic latex, polymethacrylic ester, and copolymers of these polymers.

The traceable water-repellent admixture may be introduced as a solid additive into a dry mortar mix, which may be provided as a pre-blended mixture. The pre-blended dry mortar mix typically includes sand and a cementitious binder such as Portland cement, limes, masonry cement, mortar cement, blended cement, slag cement, fly ash or other pozzolanic materials.

The term "pre-blended dry mortar mix" should not be construed as limiting and includes any mixture comprising a water-repellent admixture and a cementitious material. The pre-blended dry mortar mix may further include aggregate (such as sand), in some embodiments. The term "pre-blended" means that the water-repellent admixture is blended (combined or mixed) with a cementitious material before the cementitious material reacts as a binder for aggregate materials.

It is convenient to provide a pre-blended dry mortar mix that includes the water-repellent admixture, from a processing standpoint. Namely, it avoids the need for a mason to add a separate admixture (whether liquid or solid) to the mortar. Air entrainment may be reduced. Practically, providing a pre-blended dry mortar mix means that there is no chance that the admixture will not be present in the final material, as long as the correct dry mortar mix is used.

When a dry mortar mix is combined with water, a plastic mortar is produced. The plastic mortar is a workable paste used to bind construction blocks together and fill the gaps between them. The blocks (or other forms) may be bricks, concrete masonry units, clay masonry units, etc. Plastic mortar becomes hard when it sets, resulting in a rigid structure, or hardened mortar.

To be classified as a water-repellent admixture (i.e., additive) for masonry mortars, ASTM C1384 requires the water-uptake of the mortar (with the additive) to be less than or equal to 50% of the water-uptake of the blank mortar (without the additive) when tested in accordance with ASTM C 1403, Standard Test Method for Rate of Water Absorption of Masonry Mortars, which is incorporated by reference herein. It is desired for the water-uptake of the mortar (relative to the blank) to be less than or equal to a selected value less than 50%, such as 40%, 45%, or 48%, to assure the product will meet the 50% maximum even when allowing for variability in manufacturing.

There are a wide variety of commercial uses for traceable water-repellent admixtures provided herein. A traceable water-repellent admixture may be sold directly to another party who then combines the admixture with a cementitious material, or uses the admixture to produce a cementitious material. A traceable water-repellent admixture may be combined with a cementitious material to produce a water-repellent cementitious mortar material. A traceable water-repellent admixture, or a material containing the traceable admixture, may be combined with aggregate (e.g., sand, rocks, gravel, etc.) to produce a pre-blended dry mortar mix. A traceable water-repellent admixture may be combined with a pre-blended dry mortar mix and water to produce a masonry mortar that is plastic. A hardened mortar, formed from curing a masonry mortar, may be produced in the form of various products or disposed adjacent to concrete blocks or other forms. Combinations of any of the foregoing are possible, and other additives may be included.

In some embodiments, dry cementitious products (including Portland cement, limes, cement-lime, masonry cement, mortar cement, blended cement, slag cement, fly ash or other pozzolanic materials) used in making masonry mortars have a traceable water-repellent admixture incorporated into them. Some embodiments provide a pre-blended dry mortar mix which includes dry sand in addition to a dry cementitious material comprising a dry traceable water-repellent admixture.

A traceable water-repellent admixture may be sold to producers of dry cementitious materials (including cement-lime, masonry cement, and mortar cements) used in making masonry mortars. A traceable water-repellent admixture may be sold to producers of pre-blended dry mortars that include dry sand in addition to dry cementitious materials. These producers will, in turn, sell their products to the end user (typically a mason) who will either mix the dry cementitious material with sand and water to form a masonry mortar, or will simply add water to the pre-blended dry mortar mix to form a masonry mortar.

Traceable admixtures as disclosed herein may generally be employed as admixtures for concrete masonry units and mortar, concrete pavers, blocks, bricks, sidewalks, parking surfaces, retaining walls, grout, and other structural, functional, or ornamental forms.

EXAMPLE

In this Example, detection of bismuth in mortars is studied to assess the validity of the analytical method. A first mortar sample is a Chicago Portland Cement/Lime Mortar. A second mortar sample is a TN Masonry Cement Mortar.

Bismuth trioxide, $Bi_2O_3$, is added as a tracer in various amounts to each mortar. FIG. 1 shows data for the amount of $Bi_2O_3$ added to each sample as dry mortar (first column). All amounts are in parts-per-million (ppm). The amount of tracer as elemental bismuth (Bi) is shown in the second column. Both of the Chicago Portland Cement/Lime Mortar and the TN Masonry Cement Mortar have background levels of Bi of less than 1 ppm, according to these measurements.

During curing/hardening, hydration causes the amount of Bi to be diluted slightly (third column) because the water that is chemically bound within the cement during the hydration process increases the weight of the cured mortar compared to the weight of the uncured dry mortar mix. The fourth column of data in FIG. 1 shows analytical data employing Inductively Coupled Plasma with Mass-Spectroscopy Detector (ICP/MS) as the detection system. The fifth column is the difference between actual (analyzed with ICP/MS) and predicted (by mass balance experimentally).

FIGS. 2 and 3 show a linear regression between actual (y-axis of FIG. 3) and predicted (x-axis of FIG. 3) amounts of Bi. The correlation is very good ($r^2$=0.991, FIG. 2), indicating that the analytical method is validated and $Bi_2O_3$ can be an effective tracer in these concentration ranges for exemplary mortars.

In this detailed description, reference has been made to multiple embodiments of the disclosure and non-limiting examples relating to how the disclosure can be understood and practiced. Other embodiments that do not provide all of the features and advantages set forth herein may be utilized, without departing from the spirit and scope of the present disclosure. This disclosure incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein. Additionally, all ASTM or other standards cited herein are incorporated by reference, including all past and current versions of the standards as of the present filing date.

Where methods and steps described above indicate certain events occurring in certain order, those of ordinary skill in the art will recognize that the ordering of certain steps may be modified and that such modifications are in accordance with the variations of the disclosure. Additionally, certain of the steps may be performed concurrently in a parallel process when possible, as well as performed sequentially.

Therefore, to the extent there are variations of the disclosure, which are within the spirit of the disclosure or equivalent to the inventions found in the appended claims, it is the intent that this patent will cover those variations as well. The present invention shall only be limited by what is claimed.

What is claimed is:

1. A method of verifying the presence of a water-repellent admixture in association with a cementitious material, said method comprising:
   (a) providing a water-repellent admixture suitable for combining with a cementitious material;
   (b) providing an inorganic tracer that is substantially water-insoluble and stable in the presence of said water-repellent admixture and said cementitious material;
   (c) combining said water-repellent admixture and said inorganic tracer to form a traceable water-repellent admixture;
   (d) obtaining a sample comprising said cementitious material, in uncured or cured form; and
   (e) analyzing said sample for the presence of said traceable water-repellent admixture, by detecting said inorganic tracer in said sample in excess of native inorganic tracer concentration associated with said cementitious material,
   wherein said inorganic tracer comprises one or more rare earth metals;
   wherein said inorganic tracer is detected by a system selected from the group consisting of inductively coupled plasma, inductively coupled plasma configured with an atomic-emissions spectroscopy detector, mass-spectroscopy detector, flame atomic absorption detector, energy-dispersive X-ray spectroscopy detector, X-ray fluorescence spectrometry detector, electron-probe microanalysis detector, and combinations thereof;
   wherein said inorganic tracer is present in said sample in a concentration greater than said native inorganic tracer concentration and less than 100 ppm ("positive detection"); and
   wherein said positive detection of said inorganic tracer within said sample indicates that a step of combining said traceable admixture with said cementitious material has been performed.

2. The method of claim 1, wherein said inorganic tracer is quantified within said sample, thereby indicating that a selected amount of said traceable water-repellent admixture has been combined with said cementitious material.

3. The method of claim 1, wherein said inorganic tracer is detected or quantified within said sample and within at least one additional sample at a different sample location, thereby indicating that a selected distribution of said traceable admixture has been introduced within said cementitious material.

4. The method of claim 1, wherein said inorganic tracer is selected from the group consisting of selenium, molybdenum, bismuth, and combinations, alloys, oxides, hydrides, sulfides, carbides, salts, or derivatives thereof.

5. The method of claim 4, wherein said inorganic tracer comprises selenium or molybdenum.

6. The method of claim 4, wherein said inorganic tracer comprises bismuth or bismuth trioxide.

7. The method of claim 1, wherein the presence of said inorganic tracer does not substantially alter mechanical properties of said cementitious material.

8. The method of claim 1, wherein said inorganic tracer is stable in alkaline conditions.

9. A method of verifying the presence of an admixture, said method comprising:
   (a) providing a water-repellent admixture suitable for combining with a base material;
   (b) providing an inorganic tracer that is substantially water-insoluble and stable in the presence of said admixture and said base material;
   (c) combining said admixture and said inorganic tracer to form a traceable admixture;
   (d) obtaining a sample that may contain said traceable admixture; and
   (e) analyzing said sample for the presence of said traceable admixture, by detecting said inorganic tracer in said sample in excess of native inorganic tracer concentration associated with said admixture,
   wherein said inorganic tracer comprises one or more rare earth metals;
   wherein said inorganic tracer is detected by a system selected from the group consisting of inductively coupled plasma, inductively coupled plasma configured with an atomic-emissions spectroscopy detector, mass-spectroscopy detector, flame atomic absorption detector, energy-dispersive X-ray spectroscopy detector, X-ray fluorescence spectrometry detector, electron-probe microanalysis detector, and combinations thereof; and
   wherein said inorganic tracer is present in said sample in a concentration greater than said native inorganic tracer concentration and less than 100 ppm.

10. The method of claim 9, wherein said inorganic tracer is selected from the group consisting of selenium, molybdenum, bismuth, and combinations, alloys, oxides, hydrides, sulfides, carbides, salts, or derivatives thereof.

11. The method of claim 10, wherein said inorganic tracer comprises selenium or molybdenum.

12. The method of claim 10, wherein said inorganic tracer comprises bismuth or bismuth trioxide.

13. A method of verifying the presence of a water-repellent admixture in association with a mortar or mortar mix, said method comprising:
   (a) providing or generating a traceable water-repellent admixture comprising a water-repellent admixture and an inorganic tracer, wherein said inorganic tracer is substantially water-insoluble and stable in the presence of said water-repellent admixture and said mortar or mortar mix;
   (b) obtaining a sample comprising said mortar or mortar mix, in uncured or cured form; and (c) analyzing said sample for the presence of said traceable water-repellent admixture, by detecting said inorganic tracer in said sample in excess of native inorganic tracer concentration associated with said mortar or mortar mix, wherein said inorganic tracer comprises one or more rare earth metals;

wherein said inorganic tracer is detected by a system selected from the group consisting of inductively coupled plasma, inductively coupled plasma configured with an atomic-emissions spectroscopy detector, mass-spectroscopy detector, flame atomic absorption detector, energy-dispersive X-ray spectroscopy detector, X-ray fluorescence spectrometry detector, electron-probe microanalysis detector, and combinations thereof;

wherein said inorganic tracer is present in said sample in a concentration greater than said native inorganic tracer concentration and less than 100 ppm ("positive detection"); and wherein said positive detection of said inorganic tracer in excess of native inorganic tracer within said sample indicates that said water-repellent admixture is included in said mortar or mortar mix.

14. The method of claim 13, wherein said mortar or mortar mix is a pre-blended dry mortar mix.

15. The method of claim 13, wherein said mortar or mortar mix is a plastic mortar.

16. The method of claim 13, wherein said mortar or mortar mix is a cured hardened mortar.

17. The method of claim 13, wherein said mortar or mortar mix is a masonry mortar.

18. The method of claim 13, wherein said inorganic tracer is quantified within said sample, thereby indicating that a selected amount of said traceable water-repellent admixture has been combined with said mortar or mortar mix.

19. The method of claim 13, wherein said inorganic tracer is detected or quantified within said sample and within at least one additional sample at a different sample location, thereby indicating that a selected distribution of said traceable water-repellent admixture has been introduced within said mortar or mortar mix.

20. The method of claim 13, wherein the presence of said inorganic tracer does not substantially alter mechanical properties of said mortar or mortar mix.

* * * * *